US00PP26653P3

(12) United States Plant Patent
Brotzman

(10) Patent No.: US PP26,653 P3
(45) Date of Patent: Apr. 26, 2016

(54) DOGWOOD PLANT NAMED 'MADI-II'

(50) Latin Name: ***Cornus kousa* var. *chinensis***
Varietal Denomination: MADI-II

(71) Applicant: Timothy Charles Brotzman, Madison, OH (US)

(72) Inventor: Timothy Charles Brotzman, Madison, OH (US)

( * ) Notice: Subject to any disclaimer, the term of this patent is extended or adjusted under 35 U.S.C. 154(b) by 154 days.

(21) Appl. No.: 13/999,442

(22) Filed: Feb. 27, 2014

(65) Prior Publication Data

US 2014/0250554 P1 Sep. 4, 2014

Related U.S. Application Data

(60) Provisional application No. 61/851,143, filed on Mar. 4, 2013.

(51) Int. Cl.
*A01H 5/02* (2006.01)

(52) U.S. Cl.
USPC ..... Plt./220
CPC ..... *A01H 5/02* (2013.01)

(58) Field of Classification Search
USPC ..... Plt./220
See application file for complete search history.

*Primary Examiner* — Anne Grunberg

(57) ABSTRACT

A new variety of *Cornus kousa* var. *chinensis* named 'MADI-II' which is characterized by upright shaped habit, light green leaves becoming yellow-orange in autumn, pumpkin-yellow fruit and white flowers. In combination, these characteristics distinguish 'MADI-II' from all other cultivars known to the inventor.

3 Drawing Sheets

Genus: *Cornus.*
Species: *kousa* var. *chinensis.*
Denomination: 'MADI-II'.

BACKGROUND OF THE INVENTION

This application claims the benefit of priority under U.S.C. 119(e) of U.S. Provisional Application No. 61/851,143 filed on Mar. 4, 2013 entitled *CORNUS* PLANT NAMED 'MANDARIN JEWEL' and for which the inventor now wishes to file this application with the name or denomination 'MADI-II'.

The present invention relates to a new and distinct cultivar of *CORNUS kousa* var. *chinensis*, commonly known as Chinese or *Kousa* Dogwood, which is grown as an ornamental tree for residential and commercial landscapes. The new cultivar is known botanically as *Cornus kousa* var. *chinensis* and will be referred hereinafter by the cultivar name 'MADI-II'. The 'MADI-II' cultivar was selected in 2004 from a group of one thousand (1000) three year old *Cornus kousa* var. *chinensis* seedlings grown from open pollinated stock at Brotzman's Nursery, Inc., Madison, Ohio 44057 (41.8° N/81.06° W). Pollen parent is unknown and seed was collected from one of several large non-patented plants, none of which exhibited any of the distinct characteristics claimed by our invention. Specifically, the mother plants all produced fruit of an orange-red color, had dark green leaves which turned orange-red in autumn and exhibited a broad, spreading growth habit with dark brown twig tips. The plant being claimed, first came to our attention when it was noticed as having foliage and twigs much lighter in color than other plants of this species, including the seed source plants and the remaining seedlings within the same crop. Subsequently, this plant displayed yellow-orange autumn leaf color. First flowering occurred in 2008 and the resulting fruit were pumpkin-yellow in color, which defines the primary distinguishing trait of our new variety. Normally plants of this species have orange-red fruit. These combined characteristics suggest an apparent lack of naturally occurring anthocyanin pigments.

The 'MADI-II' variety is the only selection we are aware of that possesses these distinguishing traits. There is a plant bearing yellow fruit in Europe called *Cornus kousa* 'Xanthocarpa' (not patented). A thorough search of the literature suggests that this selection is currently not in the United States. The following selections of Chinese Dogwood, all of which produce reddish-orange fruit and reddish-orange autumn leaf color, are offered for comparison: 'Losely' U.S. Plant Pat. No. 23,423 which produces bright yellow leaves in mid-summer, flushing red: 'Madison' U.S. Plant Pat. No. 16,129 with inconsistent bright yellow leaves in mid-summer, flushing red; 'Miss Satomi' ('Satomi') (not patented) which produces red-pink flowers; 'Temple Jewel' (not patented) that produces new leaves with central yellow blotch, fading to green.

The 'MADI-II' variety was first asexually propagated by the inventor in 2006 at his nursery in Madison, Ohio. Asexual propagation was accomplished by field budding and grafting and has continued on an annual basis using the same techniques. Since that time, under careful observation, the distinguishing characteristics of 'MADI-II' have been determined stable and uniform and to reproduce true to type in successive generations of asexual propagation.

SUMMARY OF THE INVENTION

The distinguishing characteristics of 'MADI-II' are as follows: In combination these traits set 'MADI-II' apart from all other existing varieties of *Cornus kousa* and *Cornus kousa* var. *chinensis* known to the inventor. 'MADI-II' has not been tested under all possible conditions and phenotypic differences may be observed with variations in environmental, climatic and cultural conditions.

1. The fruit of 'MADI-II' are pumpkin-yellow in color.
2. The leaves of 'MADI-II' are light green in color.
3. The autumn color of the leaves of 'MADI-II' are yellow-orange.
4. The tips of the new growth of 'MADI-II' are green.
5. The habit of 'MADI-II' is upright shape when young.
6. The flowering inflorescence of 'MADI-II' are profuse, white and with partially overlapping white bracts.

DESCRIPTION OF THE DRAWINGS

The accompanying color drawings illustrate the distinguishing characteristics of 'MADI-II', namely its pumpkin-yellow fruit, light green leaves, yellow-orange autumn leaf color, upright shaped habit and profuse white flowers.

The drawing labeled

The drawing labeled

The drawing labeled

DETAILED BOTANICAL DESCRIPTION

Figure 1:
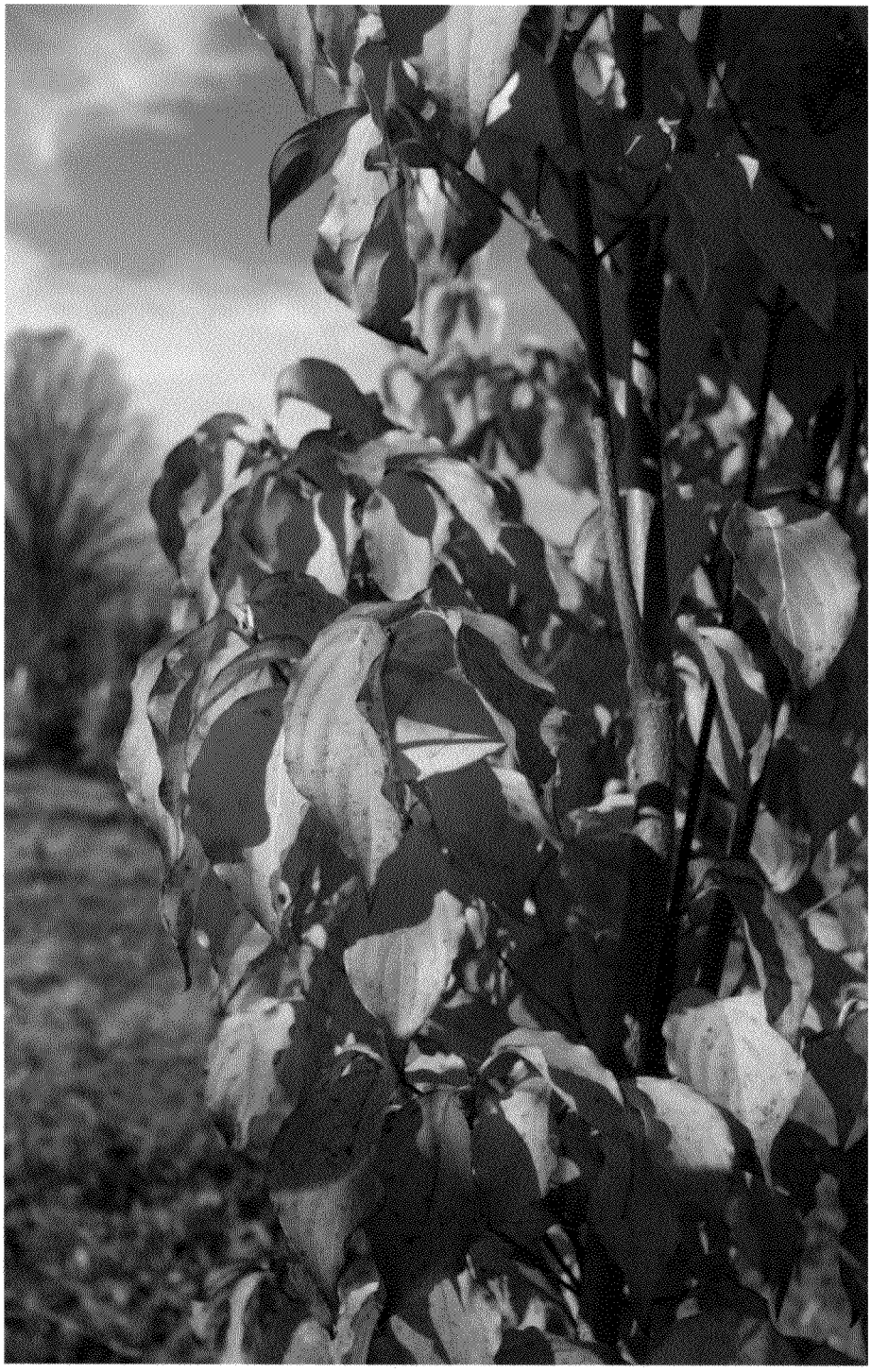
FIG. 1 depicts the yellow-orange autumn leaf color of 'MADI-II' growing in open ground, full sunlight conditions at the inventor's nursery.
Figure 2:
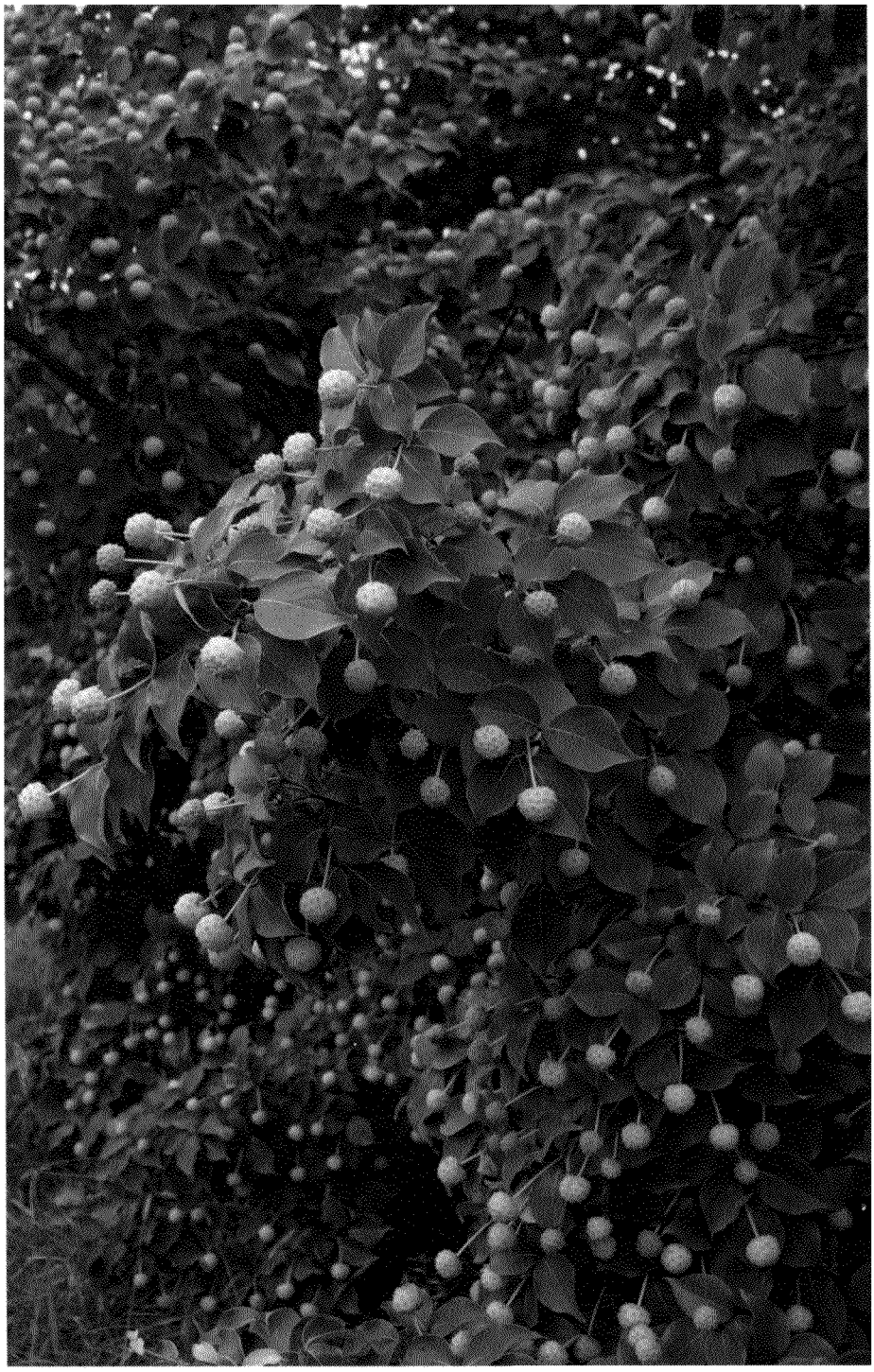
FIG. 2 depicts the pumpkin-yellow fruit of 'MADI-II' growing in open ground and full sunlight at the inventor's nursery. It also illustrates the light green leaf color and profuse flowering that has occurred.
Figure 3:
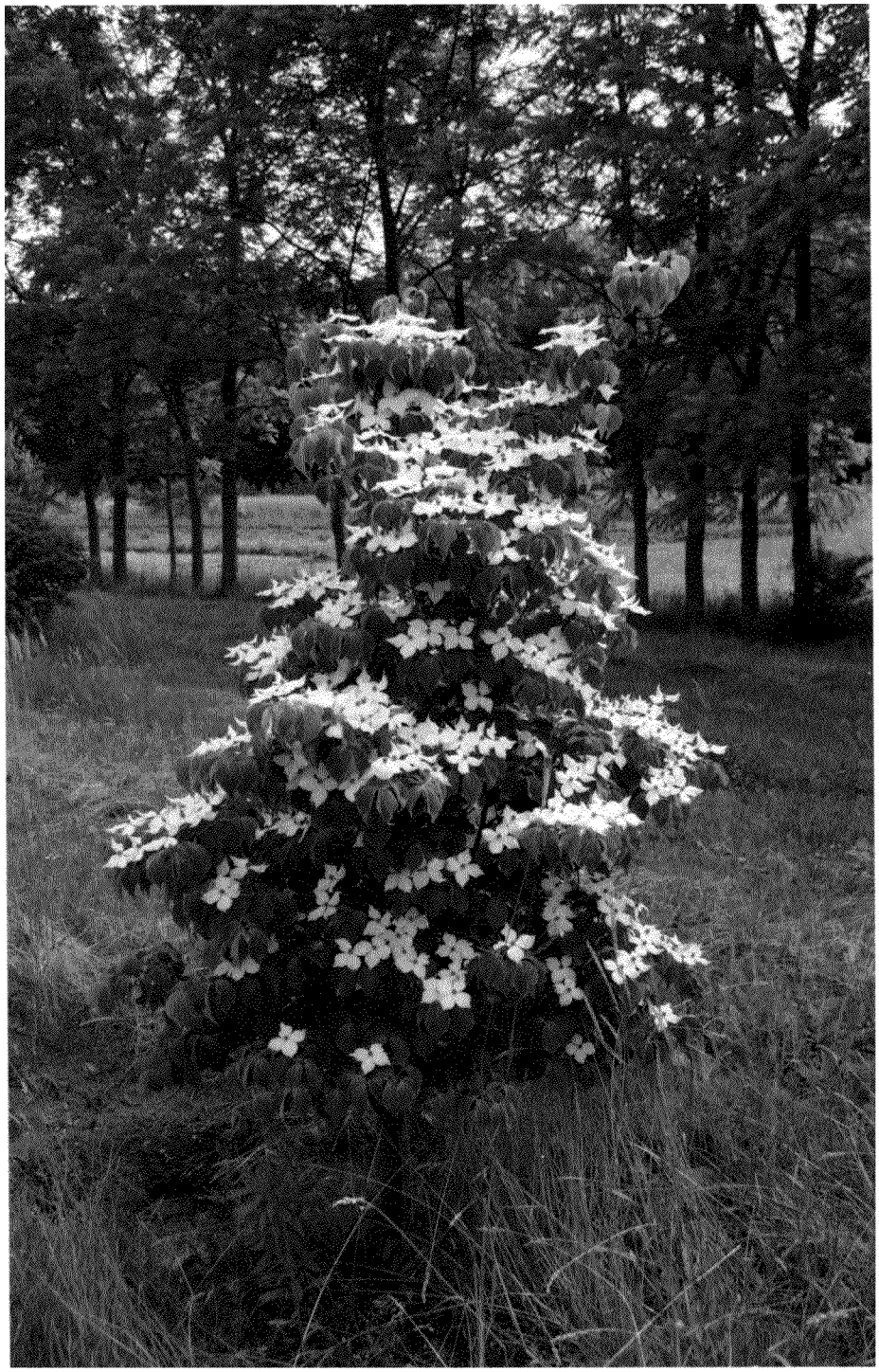
FIG. 3 depicts the upright habit of an eight year old plant of 'MADI-II' growing in open ground and full sunlight at the inventor's nursery. It also illustrates the profuse, white inflorescences of the selection.

The following is a detailed botanical description of the new and distinct variety of *Cornus kousa* var. *chinensis* known as 'MADI-II' based upon observations of eight and ten year old specimen trees which are growing at the inventor's nursery in Madison, Ohio.

'MADI-II' has not been observed under all possible environmental conditions. Where dimensions, sizes, colors and other characteristics are given, such characteristics are approximations or averages set forth as accurately as practicable. The phenotype of the variety may differ from the descriptions set forth herein with variations in environmental, climatic and cultural conditions.

The color determinations have been made by reference to the 2001 edition of The Royal Horticultural Society Colour Chart except where general color terms of ordinary dictionary significance are used.

Botanical classification:

*Family.*—Cornaceae.

*Genus.*—*Cornus.*

*Species.*—*kousa* var. *chinensis.*

Variety denomination: 'MADI-II'.

Common name: Chinese (*Kousa*) Dogwood.

Use: Specimen ornamental tree.

Cultural requirements: Well-drained, moist, acidic soil. Drought intolerant.

Light requirements: Full sun or partial shade.

Pests and disease resistance or susceptibility: No less or more resistant or susceptible to pests or diseases than the species or other cultivars known to the inventor.

Parentage: Unknown. Obtained as a seedling originating from uncontrolled pollination of *Cornus kousa* var. *chinensis* (not patented).

Hardiness: Hardy in USDA (2012) Zone 5b (−15° F.).

Size and habit: Ultimate size and shape unknown. Generally upright shaped as a young plant, the original ten year old plant is now 4 meters tall and 1.75 meters wide, more narrow at the top. Plants propagated from it have maintained this habit and proportions. Lateral branching is layered and horizontal. A wide range of factors, especially location, age and if the tree is multi-stem or single stem, influence sizes and diameters of stems and branches. It is not possible to make a predictable correlation between diameter of a primary stem and any branch arising from it. However, a primary stem with a diameter of 9 cm was observed to fork (55° crotch angle) into a smaller limb with a diameter of 6 cm at a height of 30 cm above the ground. At a height of 1.5 meters a primary stem of 6 cm was observed to fork (45° crotch angle) into limbs of 4 cm and 2.5 cm respectively, while another at the same height with diameter of 5 cm was observed to fork (30° crotch angle) into limbs of 2.5 cm and 3 cm. At a height of 3 meters, various 3 cm stems forked (25° to 30° crotch angles) into limbs averaging 1.5 cm in diameter. Young branches with diameters averaging 1 cm consistently produced lateral branches averaging 7.5 mm in diameter and crotch angles of 25°.

Growth rate: Moderate, more rapid in youth. After ten years, the original plant of 'MADI-II' has reached 4 meters in height. Annual increase to individual branches varies as to age of plant and location on the plant. Terminal locations may grow 30-45 cm annually, while laterals 18-30 cm. Under field conditions in Madison, Ohio, one year old plants produced by budding typically reach 45-75 cm in height.

Stems: Initially smooth and gray. On older trees exfoliating to reveal a patchwork of gray and tan. Whitish (Greyed-Orange Group 165-D) lenticels up to 1 mm in size, are present on all bark locations, diminishing somewhat on mature surfaces. Bark on lower trunk is of the color gray-green (Greyed-Green Group 197-A), developing gray-orange patchy exfoliation (Greyed-Orange Group 165-C) by the time the plant has reached eight years of age.

Branches: Branching is opposite. One year twigs are Greyed-Orange Group 177-B, whereas two year old branches are Greyed-Orange Group 165-A. The final 2.5-10 cm of the twig, exclusive of terminal buds is green (Yellow-Green Group 144-C).

Leaves: Deciduous, opposite, flat to slightly wavy, elliptic-ovate with acuminate tips, cuneate bases, margins entire, 8-11 cm long and 5-7 cm wide. Petiole 6-12 mm long, Green Group 137-C at time of flowering, Yellow-Orange Group 22-A in autumn. Leaf blades glabrous on top, glaucous with scattered tuffs of hair in the leaf axils underneath. Leaf venation pinnate. Newly emerging leaves in the spring exhibit yellow-green (Yellow-Green Group 144-B), darkening to green (Green Group 143-A) with lighter center vein and ribs (Yellow-Green Group 151-B). Undersides exhibit Yellow-Green Group 148-C. This is the prevailing color until the onset of autumn, when the leaves turn a yellow-orange (Yellow-Orange Group 21-A).

Buds: Are of two types—Globose, tapering flower buds averaging 9 mm in length by 5 mm in width at the base, color gray-brown (Greyed-Brown Group 199-A), and sharply tapering, triangular vegetative buds averaging 2-4 mm in length and 2 mm in width at the base, color brown (Brown Group 200-B). Immediately below most flower buds and encircling the nodes containing axillary leaf buds, either all or in part, may be found a green (Yellow-Green Group 144-C) collar approximately 3-5 mm in width.

Flowers: True flowers are four petaled, lobed, Green-Yellow Group 1-B and inconspicuous, approximately 3 mm long and 2 mm wide, 20-30 in number, found in a domed, central umbel approximately 1 cm wide and 1 cm high, simultaneously flanked by four partially overlapping, tapered, white bracts, forming a four-pointed, and symmetrical star characterizing each individual inflorescence. Calyx (sepals) not visible without magnification. Mature bracts most closely resemble Green-White Group 155-D, elliptic-ovate, flat to slightly wavy, cuneate base, margins entire, apex acuminate often curling slightly upwards. Bracts average 4.5-5.0 cm long by 3.4-4.0 cm wide, thereby producing an inflorescence with an overall width of 9.0-10.5 cm. Flowering commences last week of May to the first week of June in Madison, Ohio, lasting about 6 weeks. Depending on general vigor and cultural conditions, the typical floral display is profuse, borne towards the outside of the plant and above the foliage on green (Green Group 137-C) peduncles averaging 5.0-8.5 cm in length.

Fruits: Drupes, edible, fleshy in nature (syncarp), globose, 1.9-3.1 cm in diameter, pendulous, suspended on a 5.0-8.5 cm peduncle. Initially the peduncle closely resembles Green Group 137-C but changes to Yellow-Orange Group 22-A as fruit mature. Fruit color is atypical for the species. Newly formed fruit are green (Green Group 137-C) but by early autumn are transitioning to yellow (Yellow-Orange Group 17-B). When fully mature they are a pumpkin-yellow (Orange Group 25-A). Color of the interior pulp is lighter, Orange Group 24-A.

Seeds: Four to six per fruit, hard, round but irregular in shape, 4-6 mm in length, 3-5 mm in width.

The invention claimed is:

1. A new and distinct variety of *Cornus kousa* var. *chinensis* plant named 'MADI-II', substantially as described and illustrated herein.

* * * * *